United States Patent [19]

Atkinson

[11] Patent Number: 5,772,634
[45] Date of Patent: Jun. 30, 1998

[54] DEVICE FOR LIMITING DISTENTION FLUID PRESSURE DURING HYSTEROSCOPY

[75] Inventor: Robert W. Atkinson, Dover, Ohio

[73] Assignee: Zimmer, Inc., Warsaw, Ind.

[21] Appl. No.: 539,446

[22] Filed: Oct. 6, 1995

[51] Int. Cl.⁶ ................................................. A61M 1/00
[52] U.S. Cl. ............................................. 604/118; 604/4
[58] Field of Search ................................ 128/672, 680, 128/682; 604/4, 5, 6, 118

[56] References Cited

U.S. PATENT DOCUMENTS

| | | | |
|---|---|---|---|
| 3,456,648 | 7/1969 | Lee et al. | 604/118 X |
| 3,756,234 | 9/1973 | Kopp | 604/118 X |
| 4,098,274 | 7/1978 | Ebling et al. | 604/118 X |
| 4,406,289 | 9/1983 | Wesseling et al. | 128/672 X |
| 4,648,869 | 3/1987 | Bobo, Jr. | 604/118 X |
| 4,975,028 | 12/1990 | Schultz | 417/442 |
| 5,014,714 | 5/1991 | Millay et al. | 128/672 |
| 5,178,603 | 1/1993 | Prince | 604/4 X |

OTHER PUBLICATIONS

Ray Garry, M.D., et al.—"The Effect of Pressure on Fluid Absorption During Endometrial Ablation" *Journal of Gynecologic Surgery*, pp.1–10.

Ray Garry, M.D.—"Safety of hysteroscopic surgery" *The Lancet*, vol. 336, Oct. 20, 1990; pp. 1013–1014.

Ray Garry, M.D.—"Fluid Absorption During Laser Ablation of the Endometrium in the Treatment of Menorrhagia" *British Jornal of Anaesthesia*, Aug. 15, 1991 pp. 151–154.

*Journal of the AGLL*, (Letter to the Editor from Drs. Shirk and Gimpelson) Jun. 5, 1994.

*Primary Examiner*—Sam Rimell
*Attorney, Agent, or Firm*—Todd A. Dawson

[57] ABSTRACT

A fluid pump as used to distend a portion of a patient's body including a blood pressure monitor which preselects the maximum pressure for the pump at or slightly below the mean arterial pressure for the patient.

2 Claims, 1 Drawing Sheet

DEVICE FOR LIMITING DISTENTION FLUID PRESSURE DURING HYSTEROSCOPY

FIELD OF THE INVENTION

This invention relates to devices used to distend the uterus during hysteroscopy and has special relevance to a distention device which monitors the patient's blood pressure to set the maximum pressure of the distention pump below the mean arterial pressure.

BACKGROUND OF THE INVENTION

In recent years there has been an increasing interest in hysteroscopic endometrial ablation as an alternative treatment to hysterectomy for dysfunctional uterine bleeding. A major complication of procedures using ablation is the excessive absorption of the distending medium from the uterine cavity into the circulatory system of the patient. Several concepts have been researched and developed to reduce or otherwise limit the amount of fluid absorbed by the body as outlined in the following articles: "Fluid Absorption During Laser Ablation of the Endometrium in the Treatment of Menorrhagia," British Journal of Anaesthesia, Volume 68, pages 151–154 (1992) and "The Effect of Fluid Absorption During Endometrial Ablation," Journal of Gynecological Surgery, Volume 8, Number 1, 1992. These articles suggest limiting the pressure within the uterus to reduce the amount of fluid absorbed by the body.

SUMMARY OF THE INVENTION

The device of this invention provides a solution to the problem by setting the maximum output pressure of the distending pump at a level below the mean arterial pressure of the patient. To accomplish this task, the device includes an electronic blood pressure monitor which is connectable to the finger of a patient or other extremity pulse. The output signal from the electronic blood pressure monitor is connected to the pump control circuitry for the distention pump to establish the maximum pump output pressure. By holding the maximum distention pressure at or below the mean arterial pressure for the patient, the absorption of fluid in the circulatory system should be greatly reduced and the safety of the procedure increased.

Accordingly, it is an object of the invention to provide for a novel device for pumping a distending fluid into the body at a pressure at or below the mean arterial pressure of the patient.

Another object of the invention is to provide a distention device which monitors the blood pressure of the patient and sets the maximum distention pressure for the pump at a level at or below the mean arterial pressure of the patient.

Other objects of the invention will become apparent upon a reading of the following description taken with the accompanying drawings.

DESCRIPTION OF THE REEFERRED EMBODIMENT

Figure 1:
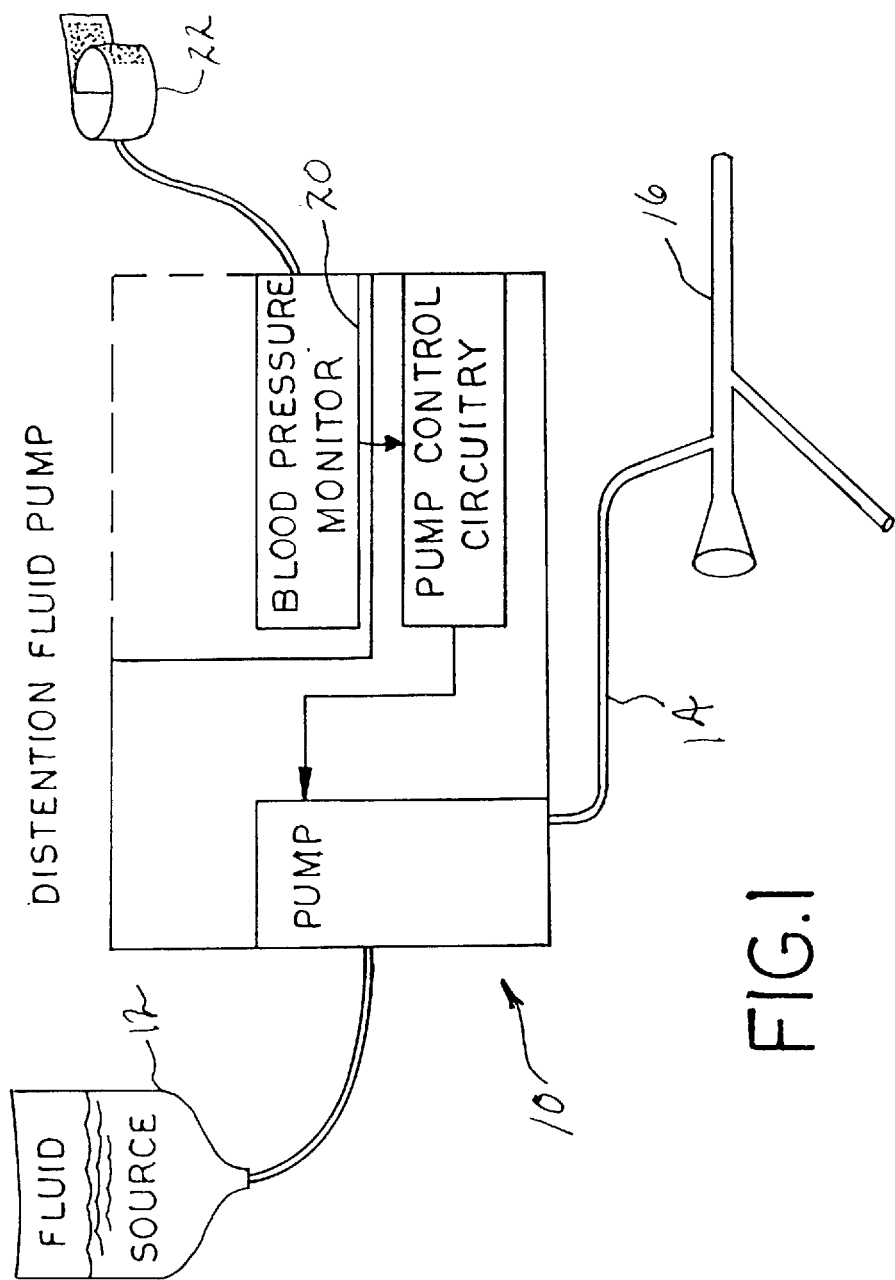
FIG. 1 illustrates the device of the invention in block diagram form.

The preferred embodiment herein described is not intended to be exhaustive or to limit the invention to the precise form disclosed. Rather, it is chosen and described to enable others skilled in the art to utilize its teachings.

FIG. 1 illustrates the invention in block diagram form as the blocks represent known technology commonly understood by persons skilled in the art. Therefore, it is not necessary to explain or illustrate each block in greater detail. Distention fluid pump 10 includes a pump for pumping a distending fluid from a fluid source 12 to the fluid inflow line 14 of a hysteroscope 16. Pump control circuitry 18 is included within the distention fluid pump for controlling the operation of the pump. The pump control circuity includes inputs (not shown) for turning on and off the pump as well as allowing the surgeon to adjust the output pressure of the pump. A blood pressure monitor 20 is provided within the distention fluid pump with its output connected to the pump control circuity. A blood pressure cuff or finger cuff 22 is connected to the input of the blood pressure monitor and is configured to be fitted about the patient. The design and operation of the blood pressure monitor is well known in the industry and need not be described further. Suffice it to say that the output of the blood pressure monitor represents the mean arterial pressure of the patient. In the subject application, the output of the blood pressure monitor is connected to the pump control circuitry so as to establish the maximum pump output pressure at or slightly below the mean arterial pressure of the patient.

In use, the pressure cuff is attached to the patient in a manner consistent with industry standards with its output connected to the input of the blood pressure monitor. A fluid source and tubing set is connected to the pump so that a fluid path is established between the fluid source and the inflow line of the hysteroscope. The distention pump is activated so that the blood pressure cuff and monitor begin to determine the mean arterial pressure for the patient, again, in a manner consistent with the industry standards. The fluid pump begins to deliver fluid to the hysteroscope at a pressure which is controlled by the pump control circuitry and at a pressure below the mean arterial pressure of the patient as determined by the blood pressure monitor.

It should be understood that the distention pump may include a number of common features such as electronic readouts, warning indicators, and a pressure adjustment control as is well known in the industry. However, according to the object of the invention, any distention of the fluid pump pressure should only be adjusted down and not upwardly above the maximum as determined by the blood pressure monitor.

It should also be understood that the blood pressure monitor may be a separate unit from the distention fluid pump having only its output connected to the pump control circuity.

Finally, it should be understood that the invention is not to be limited to the precise form disclosed but may be modified within the keeping of the appended claims.

I claim:

1. A method for controlling the maximum output pressure of a distention fluid pump, the method including the steps of:
   a: providing a fluid pump connected between a source of distention fluid and an output device configured for extending into a body cavity, wherein said fluid pump pumps fluid from the distention fluid source through the output device and into a body cavity to distend the cavity;
   b: providing a control means for controlling the operation of the fluid pump including the maximum output pressure of the pump;
   c: providing a blood pressure monitoring means adapted for connection to a patient and for producing a signal representative of the mean arterial pressure of the patient; and d: setting the maximum output pressure of the fluid pump below the mean arterial pressure of the patient.

2. The method of claim 1 wherein the blood pressure monitoring means and the control means are interconnected such that the signal representing the mean arterial pressure of the patient is sent to the control means.

\* \* \* \* \*